United States Patent [19]
Hardy

[11] Patent Number: 5,519,928
[45] Date of Patent: May 28, 1996

[54] DENTAL PRESS APPARATUS

[76] Inventor: Henry R. Hardy, 215 Rabbit Run Rd., Osteen, Fla. 32746

[21] Appl. No.: 339,079
[22] Filed: Nov. 14, 1994
[51] Int. Cl.⁶ .................................................. B23P 19/02
[52] U.S. Cl. .................................................... 29/251
[58] Field of Search .................................. 100/288, 266, 100/237, 193, 295; 29/251, 252, 282, 283, 257, 280, 263, 266

[56] References Cited

U.S. PATENT DOCUMENTS

| | | | |
|---|---|---|---|
| 535,673 | 3/1895 | Clayton | 100/266 |
| 2,336,262 | 12/1943 | Krasberg | 29/251 |
| 3,512,242 | 5/1970 | Harvis | 29/252 |
| 4,065,843 | 1/1978 | Elola | 29/252 |
| 5,176,922 | 1/1993 | Balsano et al. | 100/237 |
| 5,337,656 | 8/1994 | Hollnagel | 100/266 |

*Primary Examiner*—Robert C. Watson
*Attorney, Agent, or Firm*—William M. Hobby, III

[57] ABSTRACT

A dental press apparatus for removing and installing a dental handpiece component includes a press having a frame and a driving member supported on the frame for pushing against items placed on the press. A jig is mounted in the press frame and has a base for supporting a dental handpiece thereon and has a push plate located above the base plate and slidably mounted for sliding towards the base plate responsive to actuation of the press to move the driving member against the push plate. The first ram member attaches to the jig push plate for removing a dental handpiece member and a second ram member is attached to the push plate and is used to install a bearing onto the dental handpiece turbine. The jig base plate and push plate are held together with rods having coil springs thereover and attached to the base plate and having the push plate sliding on the rod. The spindle ram has a countersunk hole for pin alignment and the other ram member has a passageway therethrough countersunk from one end for holding a coil spring which in turn supports a hollow plunger in the barrel portion to assist in aligning and positioning a bearing being attached to the dental handpiece.

16 Claims, 1 Drawing Sheet

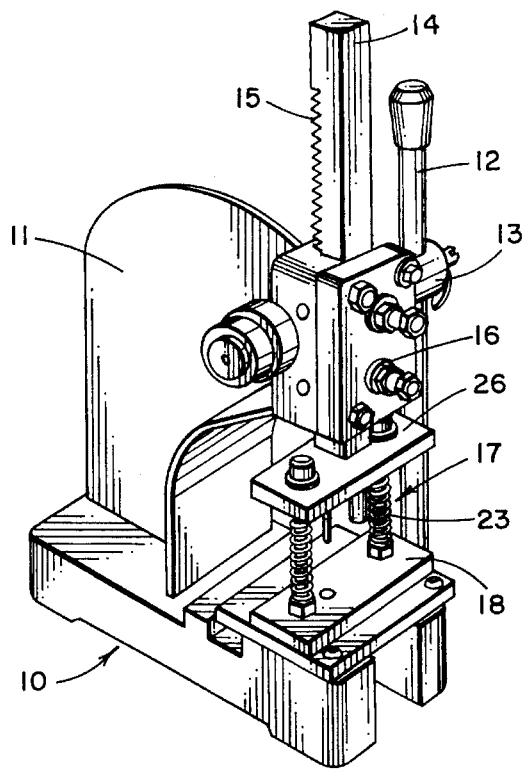
FIG. 1
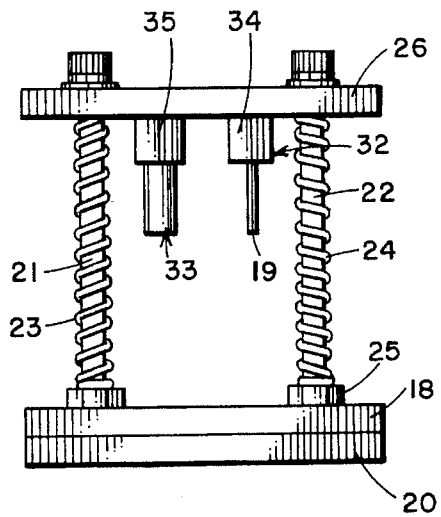
FIG. 3
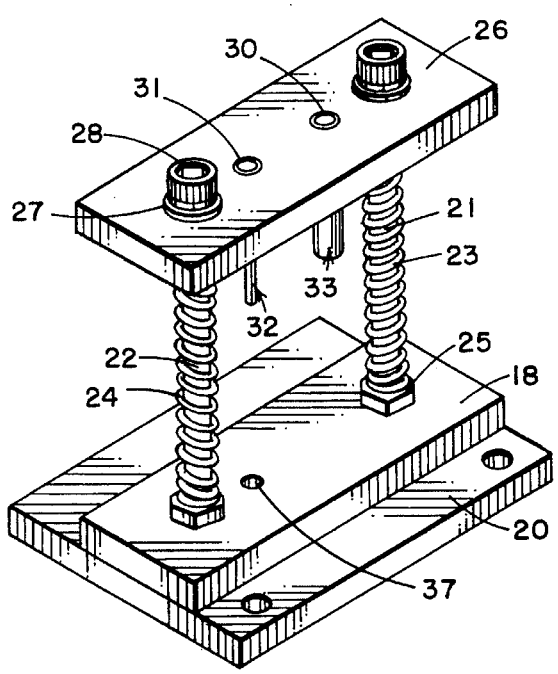
FIG. 2
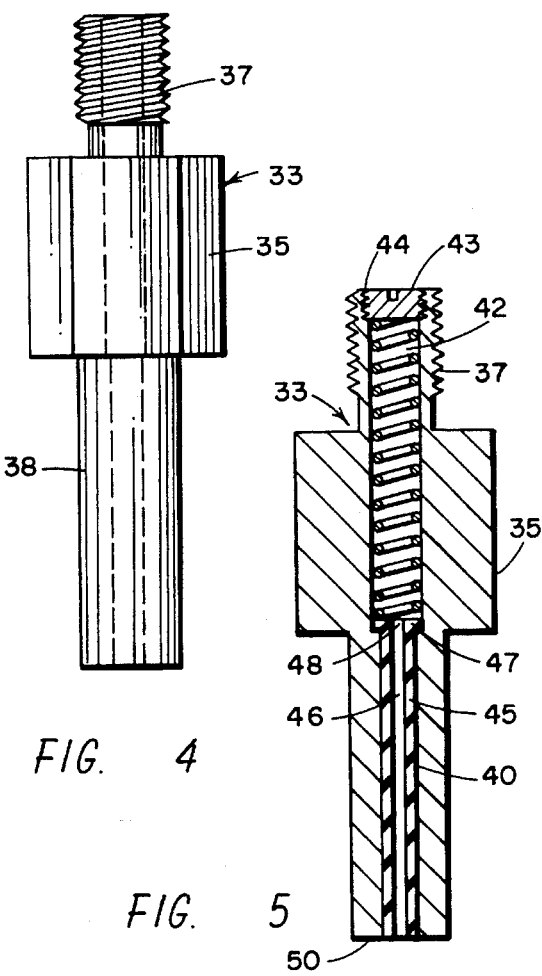
FIG. 4
FIG. 5

DENTAL PRESS APPARATUS

BACKGROUND OF THE INVENTION

The present invention relates to a dental press for removing and installing components of a dental handpiece and especially to a press having a jig therein for removing the bearing from a dental handpiece and attaching a new bearing therein.

Dental handpieces are commonly used in connection with dental instruments in the dentist's office and are typically held by the dentist while performing cleaning, drilling or other functions on a patient's teeth. The handpiece has a rotating shaft on one end which has different removable attachments for cleaning and polishing the teeth and the like. The handpiece attachments are quickly changed from one to another on the end of the rotating shaft of the handpiece. A dentist's office typically has more than one handpiece for working on patients. Dental handpieces are subject to bearing use and have to be rebuilt or repaired on a regular basis as the bearings wear out. It is common to repair such items by sending them back to the factory for either a new dental handpiece or to rebuild the worn or broke handpiece by removing and replacing the bearings. The bearings are located in the head of the handpiece and are pressed onto a spindle along with an impeller. The spindle, bearings, and impeller make up the component which the present machine rebuilds and is referred to as the handpiece turbine.

The present invention is for a small hand press having a frame which has a handle driving a gear and rack to actuate the press. A jig is designed to be placed in the press and has a base for supporting the dental handpiece turbine therein and has a push plate slidably mounted over the base and having a pair of rams attached thereon for driving a spindle from the handpiece turbine through an opening in the base plate and a second ram for forcing a new bearing onto the spindle. The press advantageously allows for the alignment of the bearings and the supporting of the bearings during the fitting of a new bearing into the handpiece turbine and in the removal of the old bearings. This allows the dentist to replace the bearings in a handpiece in his office at a small expense and thus have the use of the dental handpiece immediately rather than having to send the handpiece back to the factory to have the bearings replaced. This also substantially reduces the cost to the dentist in maintaining his equipment.

Large and small arbor and other types of presses have been common in the prior art including various types of hand presses which use a hand actuated arm rotating a gear to drive a rack, as in the present preferred embodiment. Other types of presses use a handle which acts as a lever arm to gain a mechanical advantage in driving the press while yet others use hydraulic rams to drive the press which rams are actuated by hydraulic pumps. In addition, presses and pin extractors can use a threaded shaft to gain the mechanical advantage of a screw in driving pins or components with a large mechanical force.

Prior art presses or extractors can be seen in the Pabst U.S. Pat. No. 1,800,566, for an apparatus for removing commutators from armature shafts which uses a press having a hand lever rotating a gear to drive a rack to drive a plunger for removing commutators from the armature shaft. In the Taylor U.S. Pat. No. 2,485,022, a cross-head for presses is for a manually operated arbor press using a threaded driving shaft as a press screw in the press. Similarly, the Maynard patent, No. 4,977,660, is a tool for removing and installing an automotive universal joint which has a push rod in a press for removing an automotive universal joint. The Gould U.S. Pat. No. 4,305,195, is an apparatus for disassembling and assembling skate wheels which has a pin actuated arm for driving a push/pull member for removing the bearings of a skate wheel and for reinstalling the bearings on the skate wheel. The Schneider U.S. Pat. No. 4,118,852, is for a piston pin remover and installer for use in automobile engine pistons for repair and replacement of a pair of new pins in the piston. The Miller U.S. Pat. No. 2,267,662, is for a press which uses a hydraulic jack for driving a push-type plate against a pair of springs to thereby drive a plunger. The Veilleux U.S. Pat. No. 2,629,442, is a tool for removing rivets and burrs and it has a hand actuating arm driving a cam to thereby drive a plunger.

In contrast to this prior art and the many other prior patents for various types of push/pull instruments, the present invention is for a specific press and jig for supporting and removing the bearings from a dental handpiece turbine and for holding a new bearing and reinstalling the bearing onto the handpiece turbine and uses special ram members for supporting and aligning members with the dental handpiece turbine to facilitate the rapid removal and installation of components.

SUMMARY OF THE INVENTION

A dental press apparatus for removing and installing a dental handpiece component includes a press having a frame and a driving member supported on the frame for pushing against items placed on the press. A jig is mounted in the press frame and has a base for supporting a dental handpiece thereon and has a push plate located above the base plate and slidably mounted for sliding towards the base plate responsive to actuation of the press to move the driving member against the push plate. A first ram member attaches to the jig push plate for removing a dental handpiece member, such as a bearing, and a second ram member is attached to the push plate and is used to install a bearing into the dental handpiece turbine. The jig base plate and push plate are held together with rods having coil springs thereover and attached to the base plate and having the push plate sliding on the rod. One of the ram members has a passageway therethrough countersunk from one end for holding a coil spring which in turn supports a hollow plunger in the barrel portion to assist in aligning and positioning a bearing being attached to the dental handpiece.

BRIEF DESCRIPTION OF THE DRAWINGS

Other objects, features, and advantages of the present invention will be apparent from the written description and the drawings in which:

FIG. 1 is a perspective view of a dental press in accordance with the present invention;

FIG. 2 is a perspective view of a jig to fit in the press of FIG. 1;

FIG. 3 is a side elevation of the jig of FIGS. 1 and 2;

FIG. 4 is a side elevation of a ram shown mounted to the jig fixtures of FIGS. 1–3; and FIG. 5 is a sectional view taken through the ram of FIG. 4.

DESCRIPTION OF THE PREFERRED EMBODIMENT

Referring to the drawings and especially to FIG. 1, a press 10 for removing and installing dental handpiece components, such as bearings, is illustrated having a frame 11 and a driving arm 12 which passes through a shaft member 13 which in turn drives a rotating pinion gear (not shown) which drives the rack 14, teeth 15 to move the rack 14 up and down within the gear housing 16. The press 10 has a jig 17 attached therein for use in removing and attaching bearings in a dental handpiece.

The jig, as seen in FIGS. 1–3, has a base plate 18 and mounting plate 20 supporting a pair of rods 21 and 22. Rod 21 has a coil spring 23 therearound while rod 22 has a coil spring 24 therearound. Rods 21 and 22 are threaded into a nut 25 which forms a part of a threaded base 18 which fixedly but removably attaches the rods 21 and 22 to the base 18. A push plate 26 has a pair of openings 27 therein aligned for the post 21 and 22 to pass therethrough so that the plate 26 pushes against the springs 23 and 24 and a pair of nuts 28 are attached to the threaded end of each rod 21 and 22 above the plate 26. In addition, the top plate 26 has a threaded opening 30 and 31 passing therethrough to allow for the threaded attachment of ram members. The threaded opening 30 has a ram member 33 mounted therein while the opening 31 has a ram member 32 mounted therein. Ram member 32 has a hex or wrench engagable base 34 while the ram 33 has a wrench engagable base 35. The ram 32 has a ram portion 19 which has a countersunk hole for pin alignment and, when driven, drives the plunger 19 directly into a handpiece turbine supported on the base plate 18 directly therebelow for driving the bearing spindle from the handpiece turbine through an opening 37 in the base 18. The bearing is easily removed by hand driving the press 10 by pulling the handle 12 to pull the rack 14 down against the top plate 26 to drive the top plate against the springs 23 and 24 so that the plate 26 slides on the rods 21 and 22 as it moves downward. The spindle ram 32 can be easily aligned with the handpiece turbine on the base plate 18 to drive a bearing therefrom. A new bearing can then be aligned to be driven onto the dental handpiece turbine with the bearing ram 33.

The bearing ram 33, as more clearly shown in connection with FIGS. 4 and 5, has the wrench engaging top 35 and also has a threaded portion 37 which is threaded into the opening 30 of the top plate 26 for holding the ram 33 in place. The narrowed portion 38 of the ram then extends below the hex portion 35.

As seen in FIG. 5, a bore or barrel 40 has been drilled through the ram 33 from one end to the other and a countersunk portion 41 has been drilled in from one end and holds a coil springs 42 therein which is locked under compression with the threaded cap 43 attaching into internal threads 44 in the ram member 33. The plunger member 45 slides in the barrel 40 and is a hollow member with a passageway 46 therethrough and a flange 47 at one end thereof. Flange 47 aligns with the countersunk ledge 48 to prevent the plunger 45 from extending any further than shown in FIG. 5. The hollow plunger 45 allows for the easy alignment with the bearing being pushed thereinto and which allows the plunger 45 to slide back in against the spring pressure of the spring 42 as the plunger is being driven down by the press 10 pushing the top plate 26 and the entire ram member 33 onto the handpiece being handheld within the jig 17 directly underneath the ram 33. The ram 33 with the plunger 45 is spring loaded thereinside and provides for easily alignment and attachment of a new bearing into a dental handpiece because the hollow plunger 45 allows an alignment pin on the turbine assembly to fit into the hollow portions but the hollow plunger 45 can push back into the ram 33 against the spring as the bearing is driven onto the spindle of the handpiece turbine. Once the new bearing is driven onto the handpiece turbine, the spring 23 and 24 will automatically retract top plate 26 of the jig 17 until the press is needed again.

It should be clear at this point, that a dental press has been provided which allows for the rapid removal and replacement of bearings and sleeves within the dental handpiece. However, it should also be clear that the present invention is not to be considered as limited to the forms shown which are to be considered illustrative rather than restrictive.

I claim:

1. A press for removing and installing dental handpiece components comprising:

a press having a frame and a driving member supported on said frame for pushing against items placed in said press;

a jig mounted in said press frame and having a base plate having an aperture therein for supporting a dental handpiece thereon, said jig also having a push plate located above said base plate and movably mounted toward said base plate responsive to actuation of said press to move said driving member against said push plate;

a first ram member attached to said jig push plate and aligned with said aperture in said base plate to allow a dental handpiece member to be extracted through said aperture; and a second ram member for installing a press fitting member into said dental handpiece whereby a dental handpiece can be rapidly repaired or rebuilt.

2. A press for removing and installing dental handpiece components in accordance with claim 1 in which a spring is located between said base plate and said push plate to return said push plate after actuation of said press to push said push plate toward said base plate.

3. A press for removing and installing dental handpiece components in accordance with claim 2 in which two springs are located between said base plate and said push plate.

4. A press for removing and installing dental handpiece components in accordance with claim 1 in which said push plate has a pair of threaded openings therethrough positioned for attaching said first and second rams at a predetermined location.

5. A press for removing and installing dental handpiece components in accordance with claim 4 in which said second ram member has a passageway therethrough and has a coiled spring mounted therein.

6. A press for removing and installing dental handpiece components in accordance with claim 5 in which said second ram member has an alignment plunger mounted in said passageway and spring loaded by said spring in said passageway of said second ram member.

7. A press for removing and installing dental handpiece components in accordance with claim 6 in which a threaded cap is attached over one end of said passageway in said second ram member.

8. A press for removing and installing dental handpiece components in accordance with claim 7 in which said first and second rams each have a threaded end portion for attachment to a threaded opening in said push plate.

9. A press for removing and installing dental handpiece components in accordance with claim 8 in which said first ram member is shaped to engage and remove a spindle through said opening in said base plate.

10. A press for removing and installing dental handpiece components in accordance with claim 9 in which said second ram member is shaped to attach a bearing to a dental handpiece.

11. A press for removing and installing dental handpiece components in accordance with claim 10 in which a pair of rods connect said base plate and push plate and each said rod has one said spring thereover.

12. A press for removing and installing dental handpiece components in accordance with claim 11 in which each of said pair of rods is threadedly attached to said base plate and said push plate is slidably attached to each rod.

13. A press for removing and installing dental handpiece components in accordance with claim 12 in which said press is a hand operated press having an pull arm driving a gear rack onto said push plate.

14. A press for removing and installing dental handpiece components in accordance with claim 13 in which said second ram passageway includes a countersunk portion holding a coil spring therein and has a narrower barrel portion holding said plunger therein.

15. A press for removing and installing dental handpiece components in accordance with claim 14 in which said plunger has a flanged end supported in one direction on a countersunk ledge.

16. A press for removing and installing dental handpiece components in accordance with claim 15 in which said second ram plunger is a hollow tubular member shaped to align a dental handpiece member thereunder.

\* \* \* \* \*